United States Patent [19]
Skovira

[11] Patent Number: 5,724,253
[45] Date of Patent: Mar. 3, 1998

[54] SYSTEM AND METHOD FOR SEARCHING DATA VECTORS SUCH AS GENOMES FOR SPECIFIED TEMPLATE VECTOR

[75] Inventor: Joseph Francis Skovira, Binghamton, N.Y.

[73] Assignee: International Business Machines Corporation, Armonk, N.Y.

[21] Appl. No.: 622,719

[22] Filed: Mar. 26, 1996

[51] Int. Cl.[6] .................... G06F 17/00; C12Q 1/68
[52] U.S. Cl. .................................. 364/496; 435/6
[58] Field of Search .................... 395/600, 800; 364/DIG. 2, 259, 259.2, 259.4, 242.1, 496, 499; 365/49; 435/6; 935/77

[56] References Cited

U.S. PATENT DOCUMENTS

| | | | |
|---|---|---|---|
| 2,978,675 | 4/1961 | Highleyman | 382/228 |
| 4,412,288 | 10/1983 | Herman | 128/634 |
| 4,523,278 | 6/1985 | Reinhardt et al. | 382/133 |
| 4,888,695 | 12/1989 | Shiraishi et al. | 382/129 |
| 4,965,725 | 10/1990 | Rutenberg | 382/224 |
| 5,379,420 | 1/1995 | Ullner | 395/600 |

*Primary Examiner*—George C. Elliott
*Assistant Examiner*—Robert Schwartzman
*Attorney, Agent, or Firm*—Arthur J. Samodovitz

[57] ABSTRACT

A system searches a data vector as a genome for a template vector such as a DNA fragment. The system Exclusive ORs the template vector with a like size segment of the data vector, element by element, and sums the results of the Exclusive OR operations, whereby a zero sum indicates a match and a nonzero sum indicates a lack of match. Then, the system shifts the segment one element and repeats the Exclusive ORing and Summing steps for the shifted segment. Each of the elements is represented by a respective digital value, and the values are assigned such that the result of the Exclusive ORing for each combination of elements yields a value representing the degree of mismatch between the elements in the combination.

6 Claims, 6 Drawing Sheets

SYSTEM AND METHOD FOR SEARCHING DATA VECTORS SUCH AS GENOMES FOR SPECIFIED TEMPLATE VECTOR

BACKGROUND OF THE INVENTION

The invention relates generally to cross-correlation techniques, and deals more particularly with a computerized technique for searching data vectors such as genomes for a specified template vector such as a DNA fragment.

Previously, data vectors representing data other than genomes were correlated with a template vector. For example, one such data vector is a digitized representation of a time linear communication signal and the template vector is a digitized representation of one of many expected communication signals. As another example, the data vector could be a Fourier transform, i.e. frequency spectral representation of the time linear communication signal and the template vector is a Fourier transform of one of many expected communication signals.

A cross-correlation for a time linear communication signal or frequency spectral representation has been performed as illustrated in FIG. 1. While a data vector 10 is ordinarily very long, it is shown as comprising only ten elements. A template vector 12 is shown as comprising only four elements, although this is ordinarily larger also. In this example, each element of the data vector and template vector is represented by a two bit value, although in practice the digital representation typically comprises many more than two bits. To begin the correlation or "search", the template vector 12 is aligned with the first four elements of the data vector 10 constituting the first "segment" of the data vector. Then, the first element of the template vector is multiplied (16a) with the first element of the data vector and the result is placed in an accumulator 18, the second element of the template vector is multiplied (16b) with the second element of the data vector then added to the accumulator 18, the third element of the template vector is multiplied (16c) with the third element of the data vector and added to the accumulator 18 and the fourth element of the template vector is multiplied (16d) with the fourth element of the data vector and added to the accumulator 18. The accumulated result is stored as the first element of a result vector (20). This resultant computation indicates whether or not a match occurs between the template vector and the first segment of the data vector. Then, the template is shifted one element to the right and the function is computed between the template vector and the second, third, fourth and fifth elements, i.e. the next segment of the data vector. The computations are likewise performed with progressively shifted segments of the data vector until the template vector is aligned with the last four elements of the data vector. The boundary conditions are considered next. Accordingly, the template is next aligned with the last three elements of the data vector and the first element of the data vector in this order. Then, the template is aligned with the last two elements of the data vector and the first two elements of the data vector in this order. Finally, the template is aligned with the last element of the data vector and the first three elements of the data vector in this order. These three segments form the boundary condition. The value of each result indicates the degree of match between the template and each data vector segment, and relies on "white" background noise in the data vector to yield a meaningful result.

Genetic researchers and others may need to determine if a human genome contains a specific DNA fragment. For example, it may be important to determine if a specific DNA fragment present in an experimental animal also occurs in a human. A human genome for each person comprises a sequence of pairs of nucleotides. While there are only four different nucleotides in the sequence, the entire sequence comprises up to three billion pairs of the nucleotides. Each DNA fragment comprises a specific sequence of these nucleotides; the lengths of different DNA fragments vary. A genome "contains" the DNA fragment if any segment of the genome sequence contains the same nucleotides in the same order as the DNA fragment. A prior art technique for determining if a genome contains a DNA fragment comprises an element by element search of the genome for the exact DNA fragment, although lesser degrees of match may also be significant for some applications.

The foregoing multiplication technique is not optimum for searching a genome for a DNA fragment for two reasons. First, the multiplication technique is suited to match a template to a data vector representing an ideal signal superimposed on noise whereas a digital representation of a genome would not contain any background noise. Without the noise, the multiplication will not always yield a meaningful result. Second, the multiplication operation is slow, and for DNA fragment matching, the data vector representing the human genome is so long that the processing time would be unacceptably long.

It was also previously known to divide a data vector into N head-to-tail subsequences and utilize N processors to simultaneously compare the template vector to segments within the N subsequences. This reduces the processing time by nearly a factor of N. The end boundary of each subsequence is handled by "borrowing" beginning element(s) from the next subsequence. For example, with a four element template, there are three boundary segments for each subsequence. The three boundary segments comprise the last three elements of the subsequence and the first element of the next subsequence in this order, the last two elements of the subsequence and the first two elements of the next subsequence in this order and the last element of the subsequence and the first three elements of the next subsequence in this order. While this parallel processing reduces processing time, there is still the time consuming multiplication operations to perform. Also, the multiplication operation requires "white" background noise in the data vector to yield a meaningful result, and there would be no such background noise in the genome data vector.

Accordingly, a general object of the present invention is to provide an accurate and fast system and method for searching a genome for a DNA fragment.

Another general object of the present invention is to provide a system and method of the foregoing type which is applicable to searching other types of signals or data.

SUMMARY OF THE INVENTION

The invention resides in a system for searching a data vector for a template vector. The system Exclusive ORs the template vector with a like size segment of the data vector, element by element, and sums the results of the Exclusive OR operations, whereby a zero sum indicates a match and a nonzero sum indicates a lack of match. Then, the system shifts the segment one element and repeats the Exclusive ORing and Summing steps for the shifted segment.

According to one feature of the invention, each of the elements is represented by a respective digital value, and the values are assigned such that the result of the Exclusive ORing for each combination of elements yields a value representing the degree of mismatch between the elements in the combination.

3

According to another feature of the present invention, the data vector represents a genome and the template vector represents a DNA fragment.

DETAILED DESCRIPTION OF THE PREFERRED EMBODIMENTS

Figure 2:
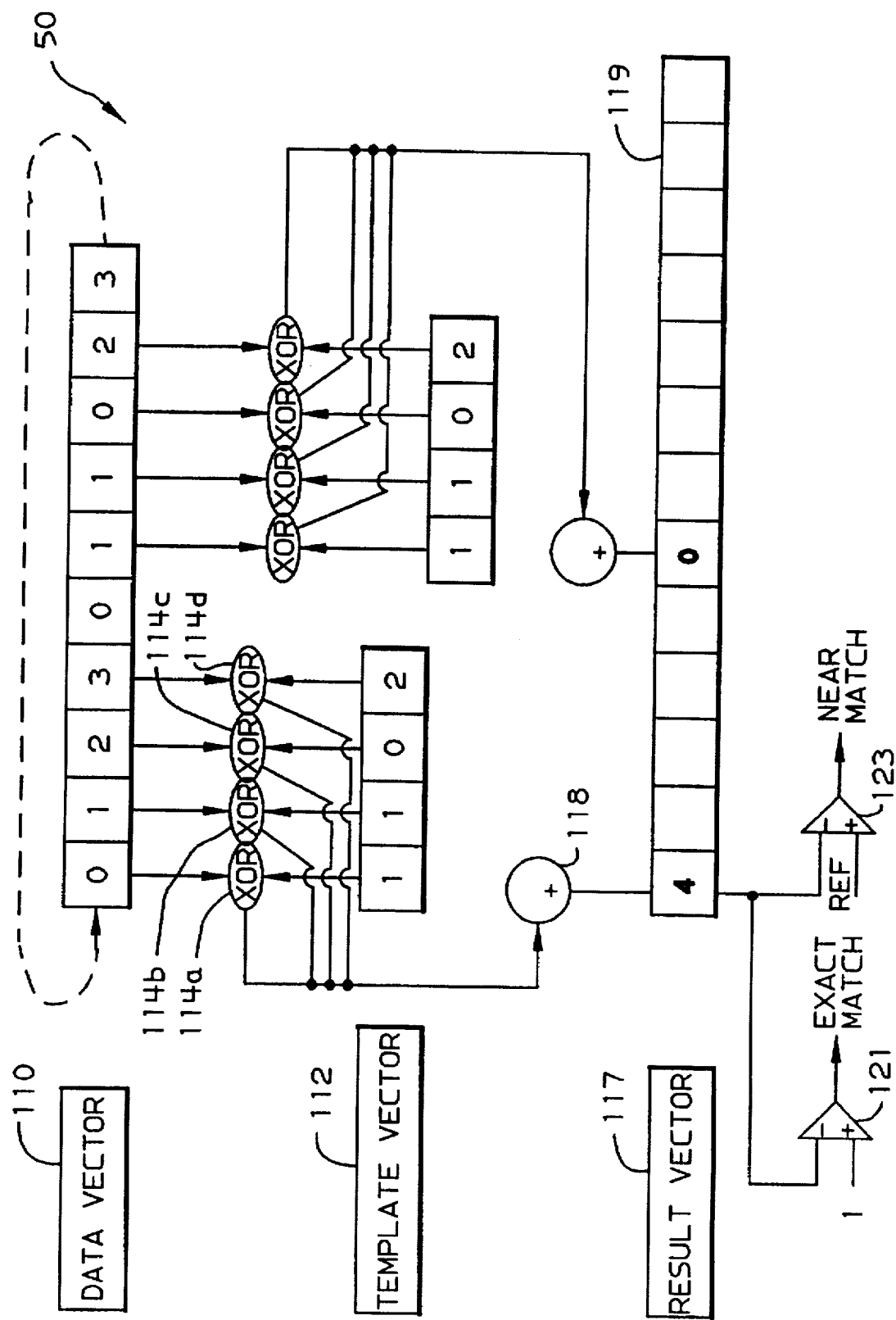
FIG. 2 illustrates a system according to the present invention for searching a genome for a DNA fragment.

Referring now to the remaining figures wherein like reference numerals indicate like elements throughout, FIG. 2 illustrates a system generally designated 50 according to the present invention for searching a human genome (or other type of data vector) for a DNA fragment (or other type of template vector). The human genome is represented by a very long digital data vector 110 (however, only ten elements are shown for purposes of explanation). Each element or box in the data vector represents one nucleotide. Because there are four possible nucleotides, two bits are required for each element. The DNA fragment is represented as a digital template vector 112 with one element or box for each nucleotide in the fragment. In the illustrated example, the DNA fragment consists of four elements and there are two bits per element to represent one of four possible nucleotides. The search comprises a "comparison" of the DNA fragment template vector to each segment of four successive nucleotides in the genome data vector. FIG. 2 illustrates comparisons of the DNA template vector to the first and sixth segments (which comparisons occur at different times by the same comparing hardware or software). The first segment comprises the first four elements of the genome data vector. The second segment is shifted one element to the right and comprises the second, third, fourth and fifth elements of the genome data vector. Each successive segment is likewise shifted one element to the right. The sixth segment comprises the sixth, seventh, eighth and ninth elements in the genome data vector. For each segment, the first nucleotide in the DNA fragment template vector is compared to the first nucleotide in the genome data vector segment, the second nucleotide in the DNA fragment template vector is compared to the second nucleotide in the genome data vector segment, the third nucleotide in the DNA fragment template vector is compared to the third nucleotide in the genome data vector segment and the fourth nucleotide in the DNA fragment template vector is compared to the fourth nucleotide in the genome data vector segment. (If the DNA fragment template vector is longer than the four elements in the example of FIG. 2, then the comparisons continue until the last of the nucleotides in the DNA fragment template vector is compared to the last nucleotide in the genome data vector segment.) Then the DNA fragment template vector is compared to the next genome data vector segment which is shifted one element to the right of the first genome data vector segment.

4

At the beginning and end of the genome data vector, the genome data vector is treated as being "wrapped" whereby the first nucleotide in the genome data vector sequence is treated as being connected to the last nucleotide in the genome data vector sequence. Thus, after the first seven comparisons of the DNA fragment template vector to the first seven genome data vector segments, the next comparison of the DNA fragment template vector is made to the last three nucleotides in the genome data vector and the first nucleotide in the genome data vector in this order, i.e. this is the eighth genome data vector segment. Next, the DNA fragment template vector is compared to the last two elements in the genome data vector and the first two nucleotides in the genome data vector in this order; i.e. this is the ninth genome data vector segment. Next, the DNA fragment template vector is compared to the last nucleotide in the genome data vector and the first three nucleotide in the genome data vector in this order; this is the tenth genome data vector segment.

The "comparisons" actually comprise Exclusive OR operations (in Exclusive OR gates or by Exclusive OR program functions, both indicated as 114a–d) where the two bit representation of each nucleotide in the genome data vector segment is Exclusive ORed with the two bit representation of the corresponding (i.e. aligned) nucleotide in the DNA fragment template vector. Thus, for the comparison of the DNA fragment template vector to the first genome data vector segment, the first element of the DNA fragment template vector is Exclusive ORed with the first element of the first genome data vector segment, the second element of the DNA fragment template vector is Exclusive ORed with the second element of the first genome data vector segment, the third element of the DNA fragment template vector is Exclusive ORed with the third element of the first genome data vector segment and the fourth element of the DNA fragment template vector is Exclusive ORed with the fourth element of the first genome data vector segment. Each Exclusive OR operation indicates a zero if the element of the DNA fragment template vector is identical to the corresponding element of the genome data vector segment; otherwise the result of the Exclusive OR operation is another integer between one and three. If there is a perfect match between the DNA fragment template vector and the genome data vector segment, then all four of the Exclusive OR operations will yield a zero. To complete the comparisons of the DNA fragment template vector to each genome data vector segment, the results of the four Exclusive OR operations (for the genome data vector segment and DNA fragment template vector) are added together (in adder 118). For a perfect match of the DNA fragment template vector to the genome data vector segment, the sum is zero. The sums are stored as a result vector in a register 119.

Because of the nature of the Exclusive Or function, the magnitude of the result vector indicates the degree of mismatch between the genome and data fragment, the higher the result vector the greater the mismatch and vice versa. A zero represents a perfect match and twelve represents the worst possible match (for this example with a four element template). The closer the value to zero the better the match and conversely the closer to twelve the worse the match. In the illustrated example, the DNA fragment template vector does not match the first genome data vector segment, and the accumulated result of the comparison is four. However, the DNA fragment template vector precisely matches the sixth genome data vector segment so the accumulated result for the sixth segment is zero.

However, if the two bit levels for each nucleotide are selected arbitrarily, then the correlation values may not be proportional to the degree of genetic mismatch between the DNA fragment template vector and the genome data vector segment. This is because the result of exclusive ORing a 01 with a 10 is three (even though the two operands are only one apart) whereas the result of exclusive ORing a 01 with a 11 is two (because the two operands are two apart). Therefore, according to the present invention, the two bit levels for each nucleotide are selected such that the result of Exclusive ORing any two combinations of nucleotides reflects the actual degree of genetic mismatch. For example, there are four different nucleotides—A, T, C and G, nucleotides A and T will bond together, nucleotides C and G will bond together but neither nucleotide A or T will bond with either nucleotides C or G. In this example, if two of the bonding nucleotides, such as nucleotides A and T are assigned two bit levels 00 and 01 respectively and the other two bonding nucleotides, such as nucleotides C and G are assigned two bit levels 10 and 11, then the results of the Exclusive Or operations between the different combinations reflect the degree of genetic similarity between the nucleotides. The following table indicates the results:

| DATA | TEMPLATE | BINARY RESULT | TEMPLATE CODE | INTEGER RESULT |
|---|---|---|---|---|
| A = 00 | 00 | 00 | A | 0 |
|  | 01 | 01 | T | 1 |
|  | 10 | 10 | C | 2 |
|  | 11 | 11 | G | 3 |
| T = 01 | 00 | 01 | A | 1 |
|  | 01 | 00 | T | 0 |
|  | 10 | 11 | C | 3 |
|  | 11 | 10 | G | 2 |
| C = 10 | 00 | 10 | A | 2 |
|  | 01 | 11 | T | 3 |
|  | 10 | 00 | C | 0 |
|  | 11 | 01 | G | 1 |
| G = 11 | 00 | 11 | A | 3 |
|  | 01 | 10 | T | 2 |
|  | 10 | 01 | C | 1 |
|  | 11 | 00 | G | 0 |

A zero result indicates a perfect match, a one result indicates one of the two close bonding relationships, either A and T or C and G, and a two or three result indicates one of the distant relationships, an A or T and a C or G. The zero and one results accurately reflect the respective degrees of match, and are correctly lower than the two and three results for the other distant relationships. However, the T and G combination and A and C combination each yields a two result whereas the A and G combination and T and C combination each yield a three result. Assuming the T and G combination and A and C combinations represent better genetic matches than the A and G combination and the T and C combination, then these results are accurate as compared to each other. Moreover, the inexpensive and fast Exclusive OR circuitry or equivalent programming described above can be used. However, if the T and G, A and C, A and G and T and C combinations all represent the same degree of genetic mismatch, then these four combinations should ideally yield the same logical result, such as two.

FIG. 2 also illustrates that each element of the result vector is compared in a digital comparator 121 (hardware or programming) to a binary one to identify exact matches between the template vector and a segment of the genome; register 119 is a shift register and incrementally advances all elements of the result vector 117 sequentially to comparator 121. Each element of the result vector is also compared in a digital comparator 123 (hardware or programming) to another binary value greater than one but small enough to indicate a substantial match between the template vector and a segment of the genome.

Alternately, the elements of the result vector can be represented by colors. For example, a zero result can be represented by the color blue and the highest result can be represented by the color yellow, and the intermediate results can be represented by a mixture of both blue and yellow such that the lower results appear more bluish, the higher results appear more yellowish and a middle result is green. Each result level is mapped to a respective mixture of blue and yellow. If desired, results above a certain level can be avoided in the display.

Figure 3:
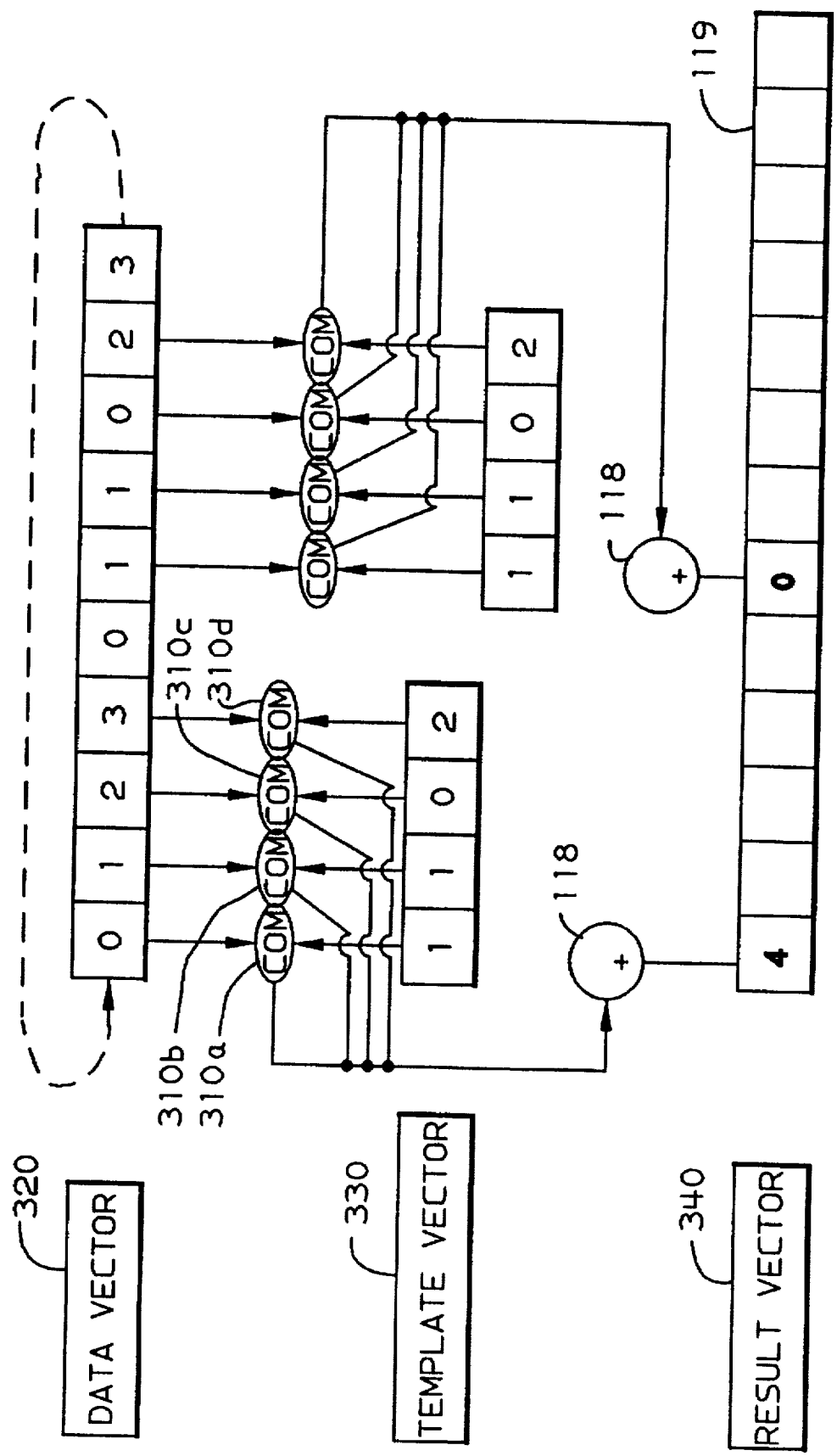
FIG. 3 illustrates an enhancement to the system illustrated in FIG. 2 to modify the weights of partial results.
Figure 4:
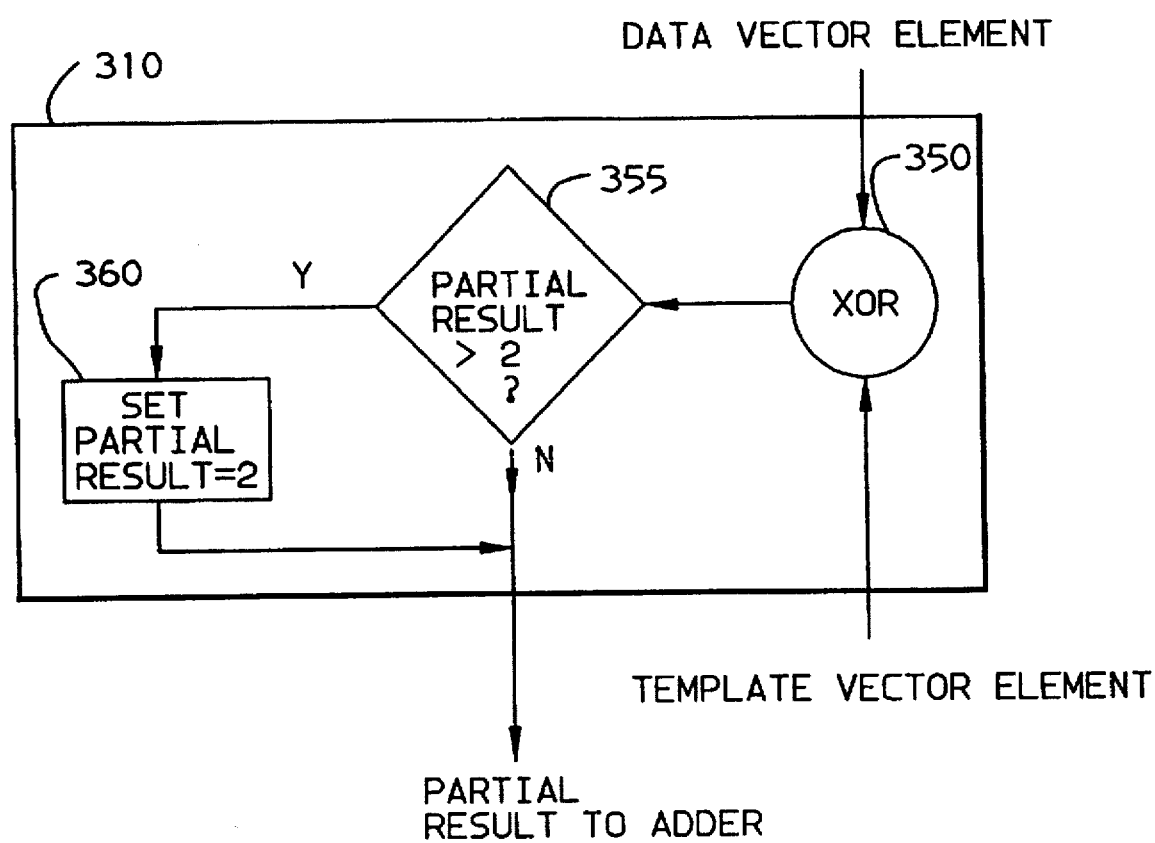
FIG. 4 illustrates more detail of the enhancement of FIG. 3.

If it is desired that the worst case pairings carry equal weight, the computation can be slightly modified as indicated in FIGS. 3 and 4. As indicated in FIG. 3, the exclusive OR is replaced with the COM comparison 310a–d. FIG. 4 illustrates that the COM comparison 300 (in either hardware or programming) includes XOR 350 and a test 355 of the partial element resulting from the XOR 350 operation. Test 355 checks for a value greater than 2. If this test is true, the value is set to 2 (step 360). This comparison has the affect of equating the weight of the partial results of 2 and 3.

Figure 1:
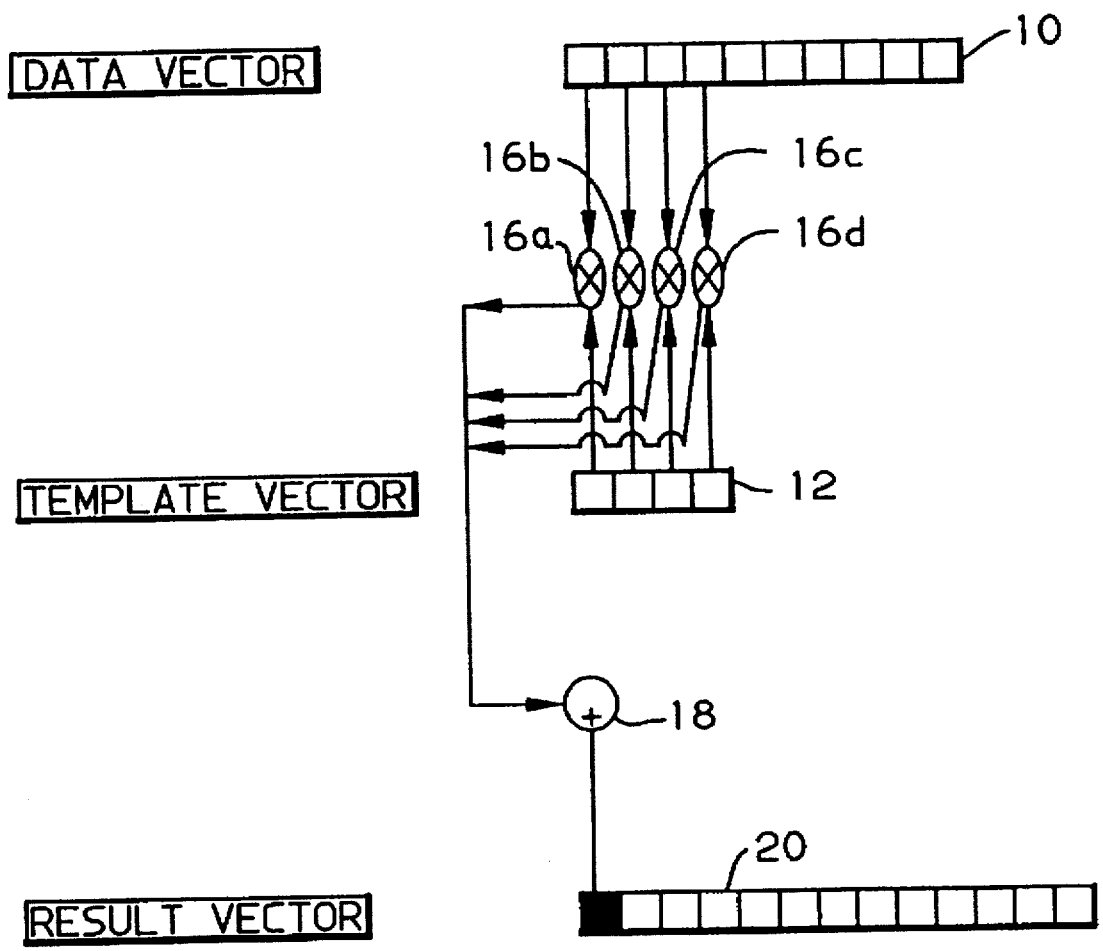
FIG. 1 illustrates a cross-correlation process according to the prior art.

The technique illustrated in FIG. 2 is faster than the technique illustrated in FIG. 1 because the technique illustrated in FIG. 2 utilizes relatively fast Exclusive OR operations instead of the relatively slow multiplication operations of FIG. 1. The technique illustrated in FIG. 2 is also more accurate than the technique illustrated in FIG. 1 because the genome data vector does not have any background noise, and the Exclusive OR operations of FIG. 2 do not require background noise to yield a meaningful result whereas the multiplication operations of FIG. 1 require background noise to yield a meaningful result.

Figure 5:
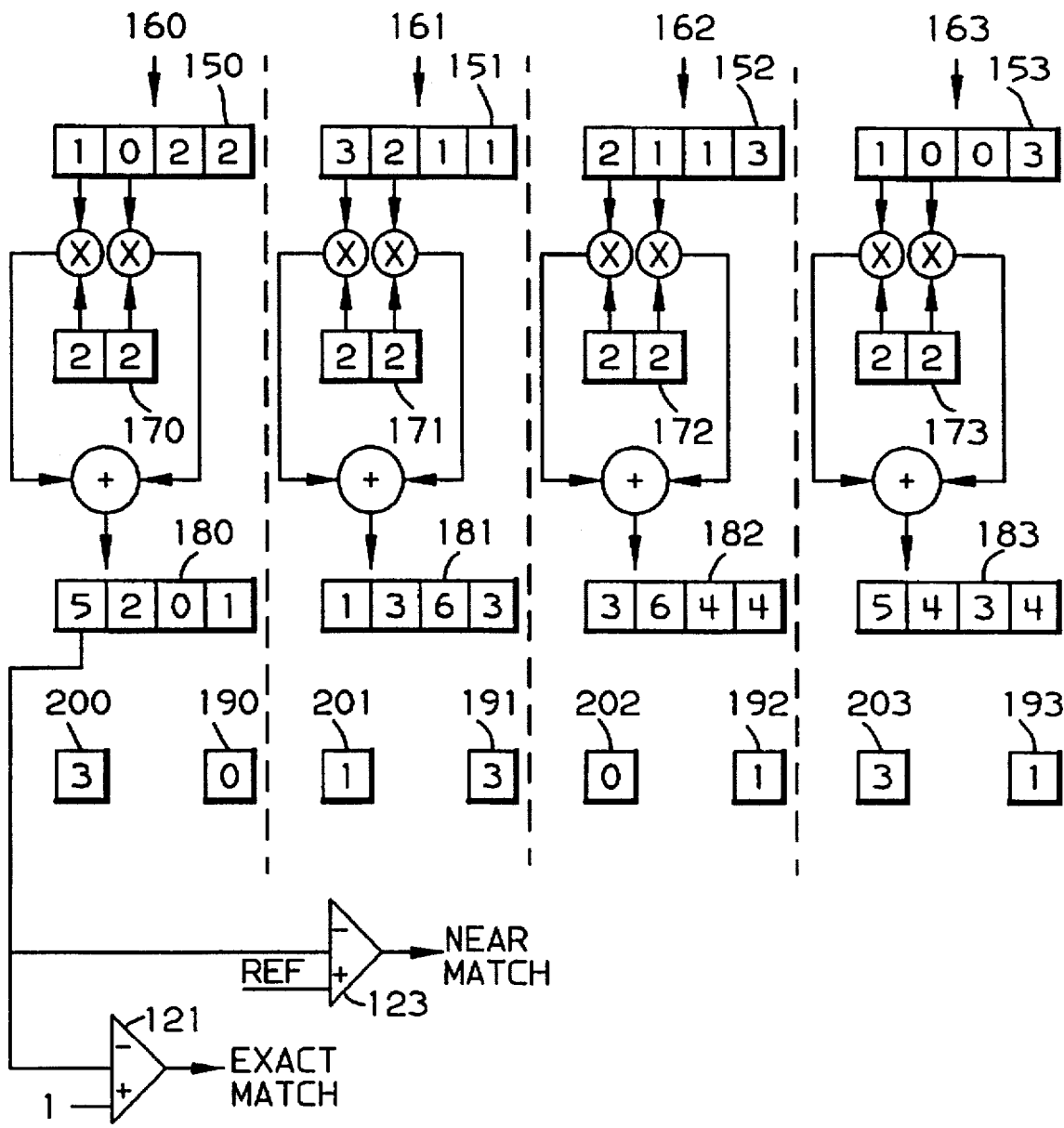
FIG. 5 illustrates another, parallel process system according to the present invention for searching a genome for a DNA fragment.

FIG. 5 illustrates a parallel processor implementation of the present invention. In the illustrated example, another genome data vector comprising sixteen elements has been divided into four "head-to-tail", four element subsequences for simultaneous processing by four processors 160–163. Each of the processors comprises a four element register 150–153, respectively. Each register stores four two bit representations of the four nucleotides in the respective subsequence. Each processor also comprises a two element register 170–173, respectively to store the DNA template vector, which in this example, is just two elements long. However, it should be noted that typically the genome data vector is much, much longer than the sixteen elements shown and the DNA fragment template vector is much longer than the two elements shown. The computations in processing 160–163 are made as follows. First, the left hand partial elements in each processor are computed. The second element of the template vector is aligned with the first element of each data vector subsequently and exclusive Ored therewith. These 4 partial results are stored in registers 200–203 respectively. Once computed, each left hand partial result is sent to the left hand neighbor. That is, processor 160 sends 200 to processor 163, 161 sends 201 to 160, 162 sends 202 to 161 and 163 sends 203 to 162. Note that this frees the registers 200–203 for future use.

Next, the results for the body of the data vector are computed. The template vector is aligned with the first two elements, i.e. the first segment of the first data vector subsequence. Then, the first element of the template vector is Exclusive ORed with the first element of the data vector subsequence and the second element of the template vector is Exclusive ORed with the second element of the data vector subsequence, and the sum of the two Exclusive OR operations is stored in the first location in a register 180. Similarly, the template vector is compared to the second and third elements of the first data vector subsequence and to the third and fourth elements of the first data vector subsequence, i.e. the second and third data vector segments. The results are stored in the second and third locations in register 180. The same operations are simultaneously performed in processors 161, 162 and 163. Thus, the first three locations in each of the registers 180–183 are filled.

Next, the right hand boundary condition is computed. The first element of the template vector is aligned with the last element of each data vector subsequence and Exclusive Ored therewith. The four "partial" results are stored in registers 190–193, respectively. Once this computation is completed, the message from the right hand neighbor is received into registers 200–201 respectively and used to complete the boundary computation. The final result for the fourth location of each register 180–183 is computed as the sum of the partial result in the respective register 190–193 plus the partial result in the next registers 200–203, respectively. For example, the result in the fourth location of register 180 equals the sum of the partial result in register 190 and the partial result in register 201 (subsequently moved to register 200) and is shown in broken line in register 180. While this yields the same result as if the first element of each data vector subsequence was borrowed for the end of the preceding data vector subsequence for the end boundary condition, the use of the partial results as described above is more efficient for long template vectors.

Figure 6:
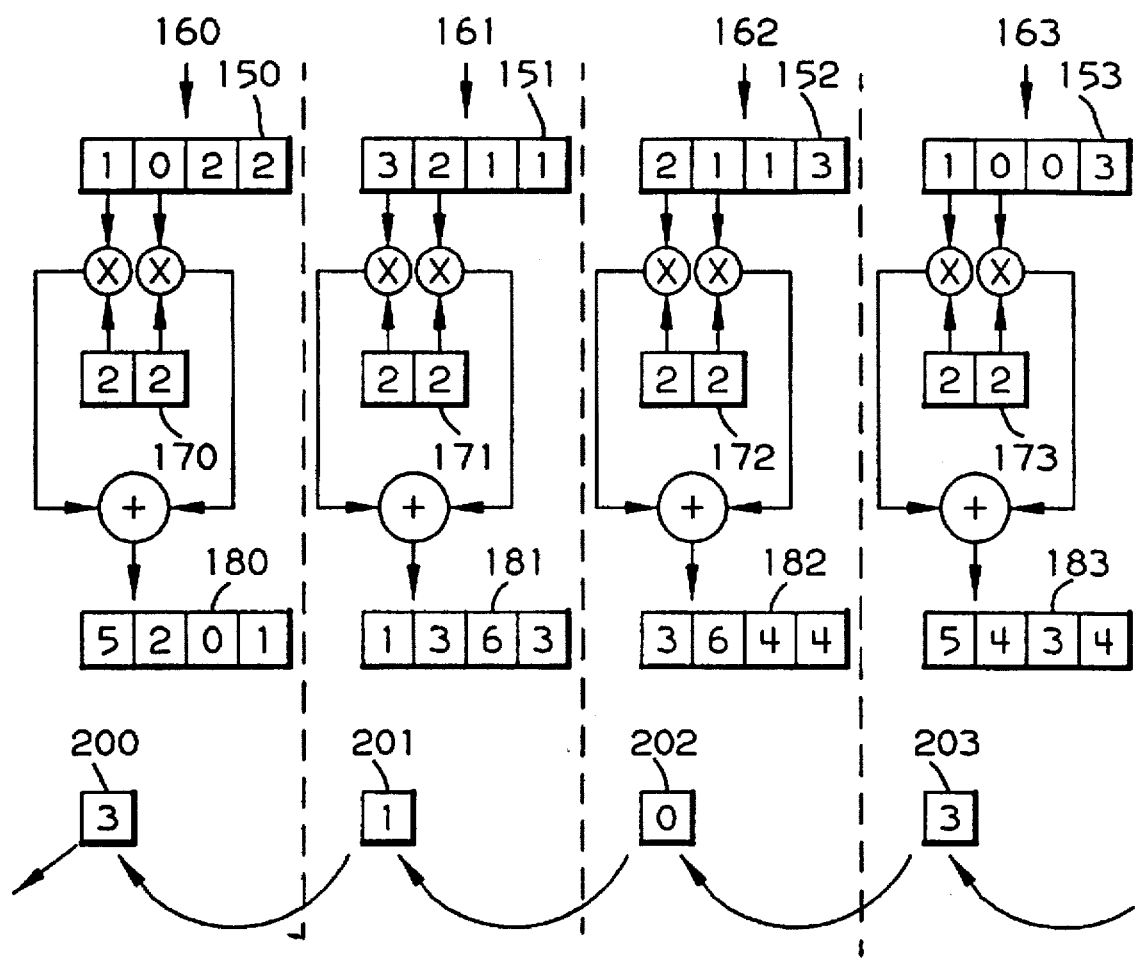
FIG. 6 illustrates an enhancement to the parallel system illustrated in FIG. 5.

As a further optimization, registers 190–193 could be eliminated as indicated in FIG. 6. In this case, the left hand boundary condition is computed and saved in registers 200–203 respectively. Then these values are transmitted to the left hand neighbors, thus freeing 200–203 for future use. When computing the right hand partial elements, the results are again stored in registers 200–203. When the message from the right hand neighbor is received, the data are stored in the last element of registers 180–183, respectively. The final elements of 180–183 are computed by adding the temporary result saved in the last element of 180–183, respectively and 190–193 and storing the results in the 4th element of 180–183. This optimization saves the register set 190–193.

The following is pseudocode for a software implementation of the foregoing parallel process:

D=Data vector of length d. The source DNA being searched.

T=Template vector of length t<<d. The DNA fragment being searched for.

P=Partial Element vector of length p=t−1. Used to store left hand partial elements.

R=Result vector of length d. Used to hold the modified correlation results.

For i=1 to p/* for all entries in the Partial Element vector */Compute one left hand partial element.
P[i]=element value
endfor At this point, vector P contains all left hand partial elements Send vector P to left hand neighbor Now compute the remaining elements of the result vector. First, compute the body of the result elements (that is, the elements that this node contains all the information for).

```
for i=1 to d−p /* For all result elements in the body section
of the computation */
    R[i]=0/* Reset one element of the result vector */
    for j=0 to t /* For all template elements */
        R[i]=R[i]+(T[j]xorD[i+j])
    endfor
endfor
```

At this point, all body elements have been computed. Now, compute the right hand partial elements

```
for i=d−t to d
    Compute one right hand partial element
    R[i] = element value
endfor
```

At this point, the right hand partial elements have been computed using the information at this node. All that remains is to add in the information from the right hand neighbor
Receive vector P from right hand neighbor.

```
for i = d−t to d
    R[i]=R[i]+P[i]
endfor
```

The computation at each node is now complete.

Based on the foregoing, a system and method for searching a genome data vector (or other type of data vector) for a DNA fragment (other type of template vector) have been disclosed. However, numerous modifications and substitutions can be made without deviating from the scope of the present invention. Therefore, the present invention has been disclosed by way of illustration and not limitation and reference should be made to the following claims to determine the scope of the present invention.

I claim:

1. A method for comparing a DNA fragment nucleotide sequence with a longer genomic nucleotide sequence, said method comprising the steps of:

representing said genomic nucleotide sequence by a first sequence of digital vector elements;

representing said DNA fragment nucleotide sequence by a second sequence of digital vector elements, said second sequence being shorter than said first sequence;

Exclusive ORing said second sequence with a like size segment of said first sequence, element by element, and Summing the results of the Exclusive ORing, whereby a zero sum indicates a nucleotide match and a nonzero sum indicates a lack of nucleotide match; and shifting said second sequence one or more elements along said first sequence and repeating the Exclusive ORing and Summing step for the shifted second sequence; and wherein each of said elements of said first and second sequences is represented by a respective digital value, and the values are assigned such that the result of the Exclusive ORing of said second sequence with each segment of said first sequence yields a value representing the degree of nucleotide mismatch between said DNA fragment nucleotide sequence and a segment of said genomic nucleotide sequence corresponding to said each segment of said first sequence.

2. The method as set forth in claim 1 wherein said second sequence has p elements, and p-1 of said segments of said first sequence comprise a last n elements and a first p-n elements of said first sequence, n varying from 1 to p-1.

3. The method as set forth in claim 1 wherein nucleotides. A and T are represented by 00 and 01 and nucleotides C and G are represented by 10 and 11.

4. The method as set forth in claim 1 wherein nucleotides A and T are represented by 10 and 11 and nucleotides C and G are represented by 00 and 01.

5. A system for comparing the nucleotide sequence of a DNA fragment nucleotide sequence with a longer genomic nucleotide sequence, said genomic nucleotide sequence being represented by a first sequence of digital vector elements, said DNA fragment nucleotide sequence being represented by a second sequence of digital vector elements, said second sequence being shorter than said first sequence, said system comprising: means for Exclusive ORing said second sequence with a like size segment of said first sequence, element by element, and Summing the results of the Exclusive ORing, whereby a zero sum indicates a nucleotide match and a nonzero sum indicates a lack of nucleotide match; and means for shifting said second sequence one or more elements along said first sequence and repeating the Exclusive ORing and Summing step for the shifted second sequence; and wherein each of said elements of said first and second sequence is represented by a respective digital value, and the values are assigned such that the result of the Exclusive ORing of said second sequence with each segment of said first sequence yields a value representing the degree of nucleotide mismatch between said DNA fragment nucleotide sequence and a segment of said genomic nucleotide sequence corresponding to said each segment of said first sequence.

6. The system as set forth in claim 5 wherein said second sequence has p elements, and p-1 of said segments of said first sequence comprise a last n elements and a first p-n elements of said first sequence, n varying from 1 to p-1.

* * * * *